(12) United States Patent
Kim et al.

(10) Patent No.: US 9,019,599 B2
(45) Date of Patent: Apr. 28, 2015

(54) LOCALIZED SURFACE PLASMON RESONANCE BASED SUPER RESOLVED TOTAL INTERNAL REFLECTION FLUORESCENCE IMAGING APPARATUS, AND DETECTION MODULE THEREFOR

(75) Inventors: Dong-Hyun Kim, Seoul (KR); Kyu-Jung Kim, Seoul (KR); Jong-Ryul Choi, Seoul (KR); Won-Ju Lee, Ansan (KR); Young-Jin Oh, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 292 days.

(21) Appl. No.: 13/581,104

(22) PCT Filed: Dec. 29, 2010

(86) PCT No.: PCT/KR2010/009519
§ 371 (c)(1),
(2), (4) Date: Oct. 30, 2012

(87) PCT Pub. No.: WO2011/105692
PCT Pub. Date: Sep. 1, 2011

(65) Prior Publication Data
US 2013/0050813 A1    Feb. 28, 2013

(30) Foreign Application Priority Data

Feb. 25, 2010 (KR) .......................... 10-2010-0017210
Aug. 31, 2010 (KR) .......................... 10-2010-0084735

(51) Int. Cl.
*G02B 21/06*    (2006.01)
*G02B 5/00*    (2006.01)
*G01N 21/64*    (2006.01)

(52) U.S. Cl.
CPC .............. *G02B 5/008* (2013.01); *G01N 21/648* (2013.01); *G01N 21/6458* (2013.01)

(58) Field of Classification Search
USPC .................. 359/385, 391; 250/227.18, 227.2; 385/12
See application file for complete search history.

(56) References Cited

U.S. PATENT DOCUMENTS 8,759,110 B2 *    6/2014    Geddes ........................... 436/94
(Continued)

FOREIGN PATENT DOCUMENTS

JP    2003-075337 A    3/2003
JP    2004-156911 A    6/2004
(Continued)

OTHER PUBLICATIONS

Sang Yun Lee et al., "Quantitative study of the gold-enhanced fluorescence of CdSe/ZnS nanocrystals as a function of distance using an AFM probe", Physical Chemistry Chemical Physics (www.rsc.org/pccp), Mar. 26, 2009, 11, pp. 4403-4409.*

(Continued)

*Primary Examiner* — Frank Font
(74) *Attorney, Agent, or Firm* — Mintz Levin Cohn Ferris Glovsky and Popeo, P.C.; Kongsik Kim; Jonathon P. Western

(57) ABSTRACT

A total internal reflection fluorescence imaging apparatus according to an embodiment of the invention includes: a metal nanostructure layer, which includes a metal thin film and a nanostructure formed over the metal thin film; a light source unit, which provides incident light such that the incident light is totally reflected off the metal nanostructure layer and an evanescent wave localized in a horizontal direction is created between the metal nanostructure layer and a specimen arranged over the metal nanostructure layer; and a fluorescence image extracting unit, which extracts and images a fluorescence signal generated by the specimen due to the evanescent wave localized in a horizontal direction.

18 Claims, 21 Drawing Sheets

(56) References Cited

U.S. PATENT DOCUMENTS

| | | | |
|---|---|---|---|
| 2005/0250094 A1* | 11/2005 | Storhoff et al. | 435/5 |
| 2005/0285128 A1* | 12/2005 | Scherer et al. | 257/98 |
| 2008/0007852 A1* | 1/2008 | Kawasaki | 359/884 |
| 2009/0263912 A1* | 10/2009 | Yang et al. | 436/164 |
| 2010/0256016 A1* | 10/2010 | Blair et al. | 506/13 |
| 2011/0015380 A1* | 1/2011 | Vezenov | 536/23.1 |
| 2013/0102770 A9* | 4/2013 | Geddes | 536/25.4 |

FOREIGN PATENT DOCUMENTS

| | | |
|---|---|---|
| JP | 2009-244018 A | 10/2009 |
| KR | 10-2002-0063587 A | 8/2002 |

OTHER PUBLICATIONS

Lee et al., "Quantitative study of the gold-enhanced fluorescence of CdSe/ZnS nanocrystals as a function of distance using an AFM probe," Physical Chemistry Chemical Physics, Mar. 26, 2009.

* cited by examiner

LOCALIZED SURFACE PLASMON RESONANCE BASED SUPER RESOLVED TOTAL INTERNAL REFLECTION FLUORESCENCE IMAGING APPARATUS, AND DETECTION MODULE THEREFOR

CROSS-REFERENCES TO RELATED APPLICATIONS

This application is a U.S. national phase application, pursuant to 35 U.S.C. §371, of PCT/KR2010/009519, filed Dec. 29, 2010, designating the United States, which claims priority to Korean Application No. 10-2010-0017210, filed Feb. 25, 2010, and Korean Application No. 10-2010-0084735, filed Aug. 31, 2010. The entire contents of the aforementioned patent applications are incorporated herein by this reference.

TECHNICAL FIELD

The present invention relates to a total reflection fluorescence imaging apparatus used as an optical measuring device for analyzing phenomena occurring in a biological specimen such as cells, more particularly to a super resolved total internal reflection fluorescence imaging apparatus and a detection module for the imaging apparatus that have a high resolution not only in the depth direction of the specimen but also in the horizontal direction.

BACKGROUND ART

A total internal reflection fluorescence (TIRF) microscope uses an evanescent wave, which is generated during a total reflection of incident light, to detect a fluorescence signal in a vertical direction for a local area of a specimen dyed with fluorescent material, and to provide the corresponding image information. The TIRF microscope is often used for research in the fields of cell biology, molecular biology, and medicine, and in particular, is used directly in research concerning various protein reactions occurring at the surface of a cell or changes in the cell surface caused by a drug.

In the basic configuration of a conventional TIRF microscope, an evanescent wave localized in a depth direction, which is created when incident light is totally reflected off the interface between a specimen and the substrate, excites the fluorescent molecules with which the specimen is dyed, and afterwards the fluorescence signal emitted by the excited fluorescent molecules is detected and imaged. However, with the conventional TIRF microscope, it is impossible, or at least difficult, to detect molecules or movement paths of molecules that are smaller than the resolution limit in the horizontal direction calculated by Abbe's diffraction equation. Thus, there is a need for a TIRF microscope that has a high resolution not only in the depth direction but also in the horizontal direction.

Technical Problem

An embodiment of the present invention provides a highly resolved total internal reflection fluorescence microscope that is capable of providing a high resolution in the horizontal direction beyond the resolution limit calculated by Abbe's diffraction equation.

Another embodiment of the present invention provides a detection module for a highly resolved total internal reflection fluorescence microscope that is capable of providing a high resolution in the horizontal direction beyond the resolution limit calculated by Abbe's diffraction equation.

Technical Solution

One aspect of the present invention provides a total internal reflection fluorescence imaging apparatus that includes: a metal nanostructure layer, which includes a metal thin film and a nanostructure formed over the metal thin film; a light source unit, which provides incident light such that the incident light is totally reflected off the metal nanostructure layer and an evanescent wave localized in a horizontal direction is created between the metal nanostructure layer and a specimen arranged over the metal nanostructure layer; and a fluorescence image extracting unit, which extracts and images a fluorescence signal generated by the specimen due to the evanescent wave localized in a horizontal direction.

The total internal reflection fluorescence imaging apparatus according to an embodiment of the present invention can further include an incident light modifying unit, which may modify a property of the incident light, where the property of the incident light can include at least one of an incident direction, an incident angle, and a wavelength of the incident light.

The incident light modifying unit can provide incident light of different properties onto the metal nanostructure layer in preset time intervals.

The incident light modifying unit can include: a first mirror configured to reflect the incident light emitted from the light source unit; a rotary mirror configured to reflect the incident light reflected by the first mirror in a first direction or a second direction by way of rotation; a second mirror positioned in the first direction and configured to reflect the incident light reflected by the rotary mirror towards the metal nanostructure layer; and a third mirror positioned in the second direction and configured to reflect the incident light reflected by the rotary mirror towards the metal nanostructure layer.

The total internal reflection fluorescence imaging apparatus according to an embodiment of the present invention can further include a transparent substrate arranged under the metal thin film and a prism arranged under the transparent substrate.

The nanostructure can include at least one of a plurality of nano-wires, nano-islands, nano-pillars, and nano-holes arrayed irregularly over the metal thin film.

The nanostructure can include at least one of a plurality of nano-wires, nano-islands, nano-pillars, and nano-holes arrayed regularly in constant intervals over the metal thin film.

The metal nanostructure layer can be formed from at least one metal material selected from a group consisting of silver (Ag), gold (Au), platinum (Pt), and aluminum (Al).

The nanostructure and the metal thin film can be formed from the same metal material.

The metal nanostructure layer can further include a metal grid formed over the metal thin film, and a plurality of nanostructures can be formed over the metal grid.

The metal grid can include a plurality of stripe-shaped grid structures arrayed parallel to one another over the metal thin film.

The metal grid can be formed from at least one metal material selected from a group consisting of silver (Ag), gold (Au), platinum (Pt), and aluminum (Al).

The plurality of nanostructures and the metal grid can be formed from the same metal material.

Another aspect of the present invention provides a detection module that includes a metal nanostructure layer having a metal thin film and a nanostructure formed over the metal thin film, where incident light is totally reflected off the metal nanostructure layer so that an evanescent wave localized in a horizontal direction is created between the metal nanostructure layer and a specimen arranged over the metal nanostructure layer.

Advantageous Effects

According to certain embodiments of the present invention, it is not only possible to have the total reflection of incident light produce an evanescent wave localized in a vertical direction of a specimen, but also it is possible to localize the evanescent wave in a horizontal direction, using the phenomenon of localized surface plasmon resonance, thereby enabling the detection of fluorescence signals by exciting fluorescent molecules in a specimen area localized in the vertical direction and the horizontal direction. Thus, a TIRF microscope according to an embodiment of the present invention can maintain a high resolution property in the vertical direction, just as in the conventional TIRF microscope, but can also provide a high resonance property in the horizontal direction. As such, a TIRF microscope according to an embodiment of the present invention can be used in a molecular biological aspect and in a medical aspect to effectively observe the movement of proteins having sizes of several tens of nanometers, in order to analyze and treat causes of diseases such as cancer cells, etc., and to effectively study the distribution and movement of matter within the body, such as viruses, having very small sizes (e.g. within 100 nanometers), which were hitherto difficult to analyze.

MODE FOR INVENTION

Figure 1:
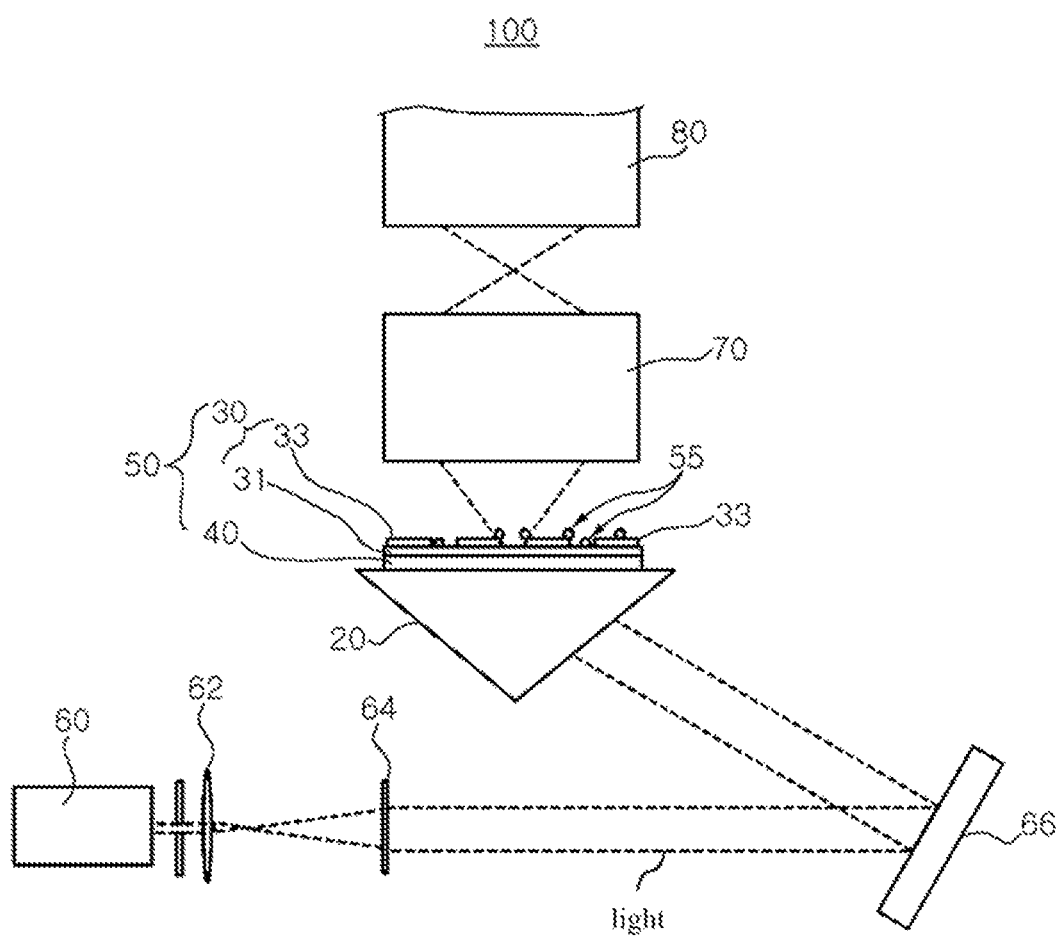
FIG. 1 schematically illustrates a TIRF microscope according to an embodiment of the present invention.

A total internal reflection fluorescence (TIRF) imaging apparatus according to an embodiment of the present invention may have an optical arrangement that induces the surface plasmon resonance phenomenon in order to obtain a high resonance in a horizontal direction. The optical arrangement may generate evanescent waves, which are created by incident light under conditions that provide total internal reflection, in a local area in a vertical and a horizontal direction. The optical arrangement may include a transparent substrate such as a glass substrate, a metal thin film formed over the substrate, and metal nanostructures (e.g. nano-wires, nano-islands, nano-holes, nano-pillars, etc.) arrayed irregularly or arrayed regularly in constant intervals over the metal thin film.

A TIRF imaging apparatus can be a TIRF microscope. While the present invention will be described below for examples in which the apparatus according to certain embodiments of the present invention is a TIRF microscope, the invention is not thus limited, and an apparatus based on surface plasmon resonance, such as a sensor apparatus, etc., can be included within the scope of the present invention.

The conditions for the metal nanostructures optimized for localization in the vertical direction and horizontal direction of the evanescent waves can be determined depending on the type of metal used in the optical arrangement, the wavelength of the light source, and the incident angle of the incident light.

The conditions for the metal nanostructures can be obtained by way of RCWA (rigorous coupled wave analysis) or FDTD (finite difference time domain) calculations. The method of forming the metal nanostructures on the metal thin film can employ processes used in semiconductor integration, such as e-beam lithography, etc.

Certain embodiments of the present invention will be described below in more detail with reference to the accompanying drawings. However, the scope of the present invention is not limited to the embodiments described below. The shape, size, etc., of the elements shown in the drawings may be exaggerated for clearer explanation, and elements indicated by the same numerals in the drawings represent the same element.

FIG. 1 schematically illustrates a TIRF microscope according to an embodiment of the present invention. The TIRF microscope 100 may include a light source unit 60, a fluorescence image extracting unit 80, and an optical arrangement 50, 20 where the excitation light emitted from the light source unit 60 arrives and undergoes total reflection. By way of the optical arrangement 50, 20, an evanescent wave may ultimately be created over a prism 20 or a lens having a high numerical aperture; and at the position where the evanescent wave is created, the metal nanostructure layer 30 may be arranged, and a specimen 55 such as a biological sample may be loaded over the metal nanostructure layer 30.

Referring to FIG. 1, the optical arrangement 50, 20 used in the TIRF microscope 100 may include a detection module 50 for the TIRF microscope and a prism 20 arranged underneath. The detection module 50 may include a transparent substrate 40, such as SF10, etc., and a metal nanostructure layer 30 formed over the transparent substrate 40. The metal nanostructure layer 30 may include a metal thin film 31 formed over the transparent substrate 40, and a multiple number of metal nanostructures 33 formed over the metal thin film 31. The metal nanostructures 33 can be, for example, metal nano-wires, nano-islands, nano-holes, or nano-pillars arrayed irregularly. In another embodiment, the metal nanostructures 33 can be metal nano-wires, nano-islands, nano-holes, or nano-pillars arrayed regularly in constant intervals. The metal thin film 31 and the metal nanostructures 33 can be formed from the same metal material. The metal nanostructure layer can be formed, for example, from at least one metal material selected from a group consisting of silver (Ag), gold (Au), platinum (Pt), and aluminum (Al).

The light source unit 60 can use a helium-cadmium laser light source that emits incident light having a wavelength of 442 nm, or an argon-ion laser light source that emits incident light having a wavelength of 488 to 532 nm, or a helium-neon laser light source that emits incident light having a wavelength of 632.8 nm.

As further described later, the metal nanostructures 33 formed over the metal thin film 31 can generate a localized surface plasmon resonance phenomenon for electromagnetic waves (incident light) that is incident under surface plasmon resonance conditions, and can concentrate electromagnetic waves (evanescent waves) for an area localized in a horizontal direction. This phenomenon of concentrating electromagnetic waves is referred to as electromagnetic wave enhancement in a localized area caused by surface plasmon resonance (localized surface plasmon enhancement).

According to an embodiment of the present invention, the evanescent wave created between the metal nanostructure layer 30 and the specimen 55 by incident light undergoing total reflection may be localized not only in the vertical direction of the specimen but also in the horizontal direction by the localized surface plasmon resonance described above. Due to the evanescent wave localized in the vertical direction and horizontal direction by the surface plasmon resonance phenomenon, the fluorescent material with which the specimen 55 is dyed may be excited, resulting in an emission of a fluorescence signal. This fluorescence signal can provide a resolution higher than the resolution limit calculated by Abbe's diffraction equation for the horizontal direction.

Looking at an example in which a helium-neon laser light source is used for the light source unit 60, a helium-neon laser of a 632 nm wavelength may be emitted from the light source unit 60, may pass through a beam expander 62, and may be polarized by a polarizer 64 into a TM mode. Optical devices such as a reflector mirror 66, etc., can be used to obtain the incident angle for the incident light with which total reflection occurs. The incident light having an incident angle required for total reflection may arrive at the prism 20 of the optical arrangement 50, 20 and pass through the transparent substrate 40 such as a glass substrate, etc., to be totally reflected at the metal thin film 31 having nanostructures 33 positioned thereon (nano-wires, nano-islands, nano-holes, nano-pillars, etc., arrayed irregularly or arrayed regularly in constant intervals). With the total reflection, an evanescent wave may be created between the metal nanostructure layer 30 and the specimen. In particular, due to the metal nanostructure layer 30, a surface plasmon resonance phenomenon may occur, so that the evanescent wave localized in the horizontal direction may excite the fluorescent particles, and the excited fluorescent particles may emit fluorescent light. The fluorescent light thus emitted may pass through an object lens 70 and a band-pass filter (not shown) for enhancing contrast sensitivity, to be detected in a 2-dimensional form by the fluorescence image extracting unit 80.

In the TIRF microscope 100 of FIG. 1, the refractive index may differ depending on the materials of the prism 20 and the transparent substrate 40, and therefore, the conditions for the metal nanostructures 33 and metal thin film 31 optimized for the localization of the evanescent wave in the vertical and horizontal directions may differ depending on the materials of the prism 20 and the transparent substrate 40. Also, by further arranging an index-matching liquid or gel between the prism 20 and the transparent substrate 40, any mismatching of the refractive index caused by air gaps that may occur between the prism 20 and the transparent substrate 40 can be avoided.

In the TIRF microscope 100 of FIG. 1, it is also possible to omit the prism 20 and instead arrange the object lens 70 at the position of the prism 20. For example, an object lens 70 having a numerical aperture of 0.8 or higher can be arranged under the transparent substrate 40 (with the prism omitted) to totally reflect incident light. In this case, the fluorescence image extracting unit 80 may be arranged under the object lens 70 and may detect the fluorescent light emitted due to the evanescent wave localized in the vertical and horizontal directions from under the transparent substrate 40.

Figure 2:
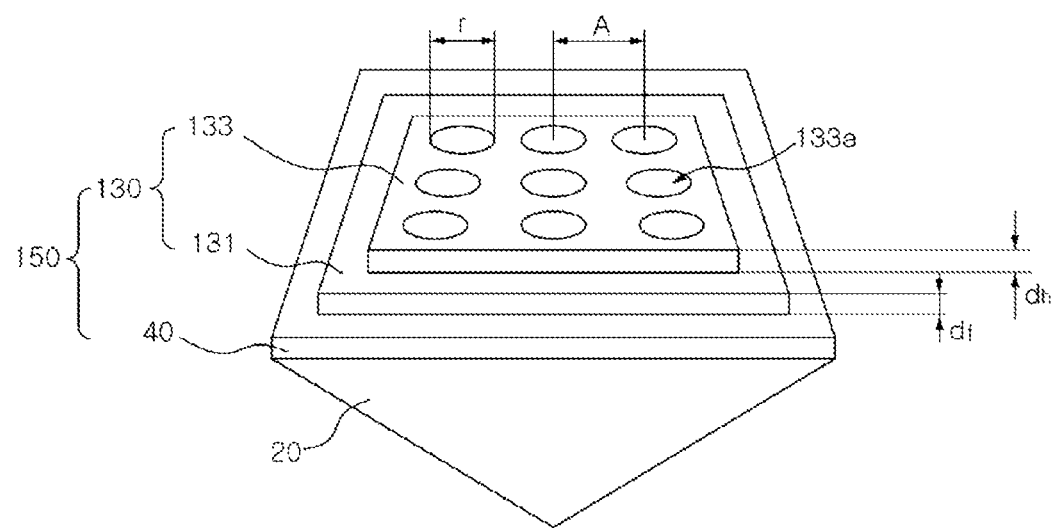
FIG. 2 illustrates an optical arrangement including a metal nanostructure for generating surface plasmon resonance that can be applied to a TIRF microscope according to an embodiment of the present invention.

FIG. 2 illustrates an optical arrangement including a metal nanostructure for generating surface plasmon resonance that can be applied to a TIRF microscope according to an embodiment of the present invention. FIG. 2 schematically shows nano-holes 133a arrayed in constant intervals (A), as one example of metal nanostructures that can generate the surface plasmon resonance phenomenon with incident light under conditions that cause total reflection and can thereby localize the evanescent wave in the vertical direction and the horizontal direction. The nano-holes 133a arrayed in constant intervals (A) may each have a constant thickness (dh) and radius (rh), and the metal thin film 131 below the nano-hole structure may also have a constant thickness (df). The metal nanostructure layer 130, i.e. the metal structure 133 having the nano-holes and the metal thin film 131 underneath, can be formed from the same metal material, and can be formed from a metal material such as silver (Ag), gold (Au), platinum (Pt), aluminum (Al), etc. The transparent substrate 40 and the prism 20 may be arranged under the metal thin film 131, where the transparent substrate 40 and the prism 20 can be made of the same material. A metal film for enhancing adhesion, such as a Cr film, for example, can be additionally included between the transparent substrate 40 and the metal thin film 131. The detection module 150 for the TIRF microscope can include the transparent substrate 40 and the metal nanostructure layer 130 formed over the transparent substrate 40 and can be provided in the form of a separate part.

Figure 3:
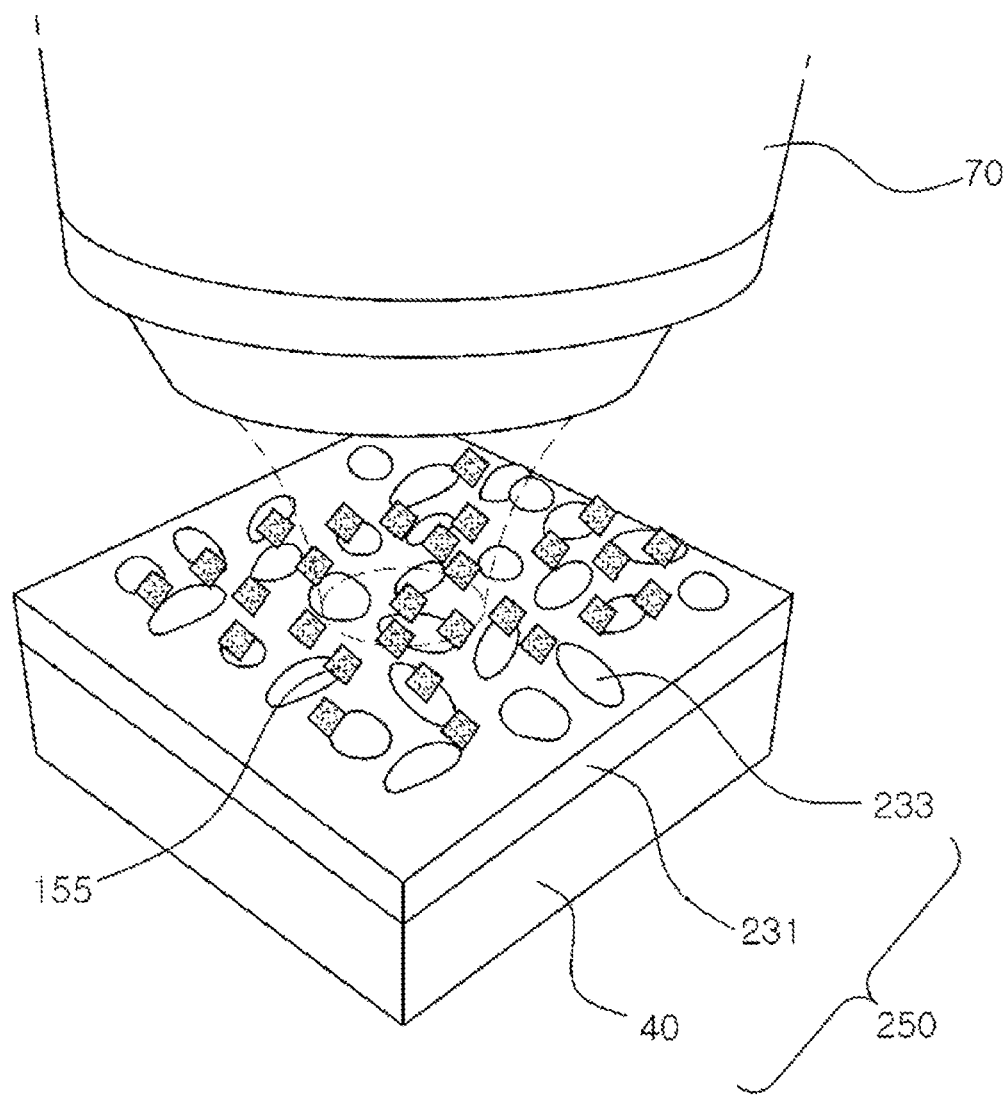
FIG. 3 schematically illustrates an imaging scheme using irregularly arrayed nano-islands that can be applied to a TIRF microscope according to an embodiment of the present invention.

FIG. 3 schematically illustrates an imaging scheme using irregularly arrayed nano-islands that can be applied to a TIRF microscope according to an embodiment of the present invention. The fluorescent material excited to a localized portion may be imaged in the portion (illustrated in dotted lines) where the object lens 70 creates a focus in a size greater than Abbe's diffraction limit, resulting in a resolution that is improved compared to the fluorescent material of the overall portion in existing TIRF microscope methods. The detection module 250 may include the metal thin film 231, the nano-islands 233, and the transparent substrate 40. In FIG. 3, the reference numeral 155 represents a specimen, such as a virus, etc.

Figure 4:
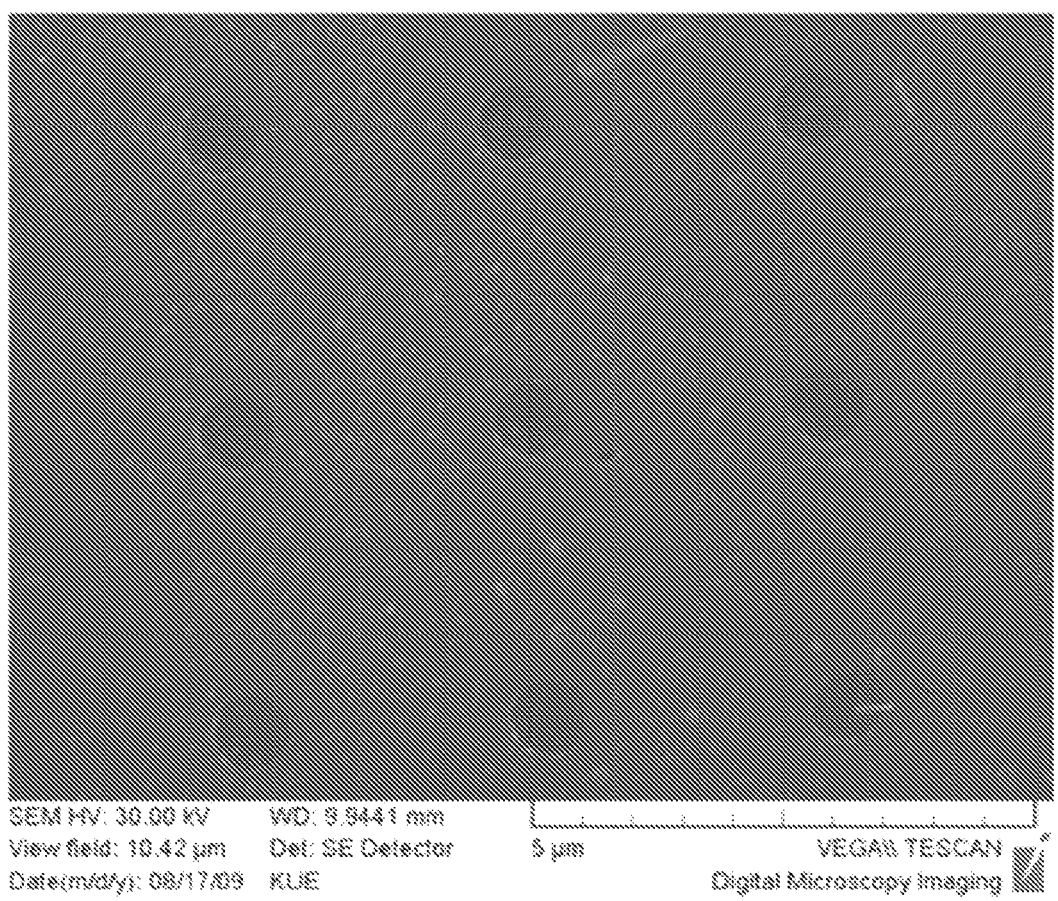
FIG. 4 is an SEM (scanning electron microscopy) photograph illustrating regularly arrayed metal nano-holes that can be applied to a TIRF microscope according to an embodiment of the present invention.

FIG. 4 is an SEM (scanning electron microscopy) photograph illustrating regularly arrayed metal nano-holes that can be applied to a TIRF microscope according to an embodiment of the present invention. The regularly arrayed nano-holes can be fabricated, for example, by using e-beam lithography over a silver (Ag) thin film.

Figure 5:
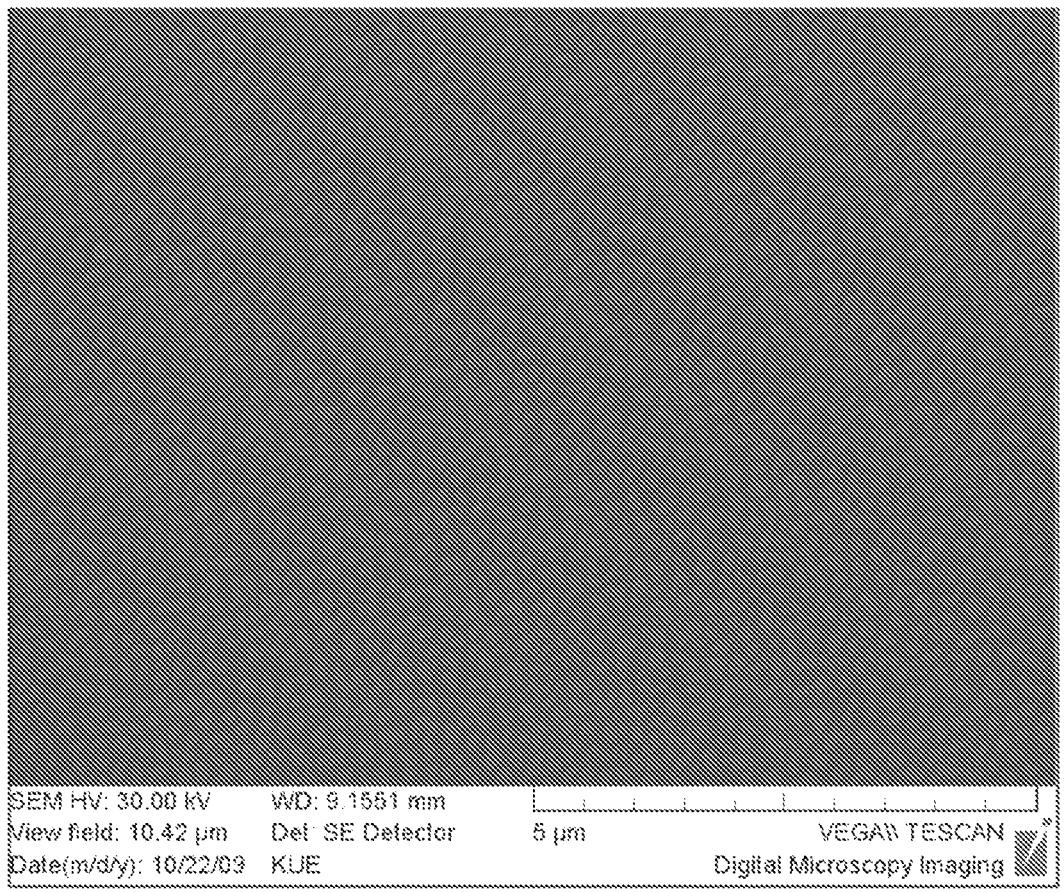
FIG. 5 is an SEM photograph illustrating irregularly arrayed metal nano-islands that can be applied to a TIRF microscope according to an embodiment of the present invention.

FIG. 5 is an SEM photograph illustrating irregularly arrayed metal nano-islands that can be applied to a TIRF microscope according to an embodiment of the present invention. The irregularly arrayed metal nano-islands can be easily fabricated, for example, by forming a metal layer made of silver (Ag) over a silver (Ag) thin film and heating to a temperature of 150 to 200° C.

Figure 6:
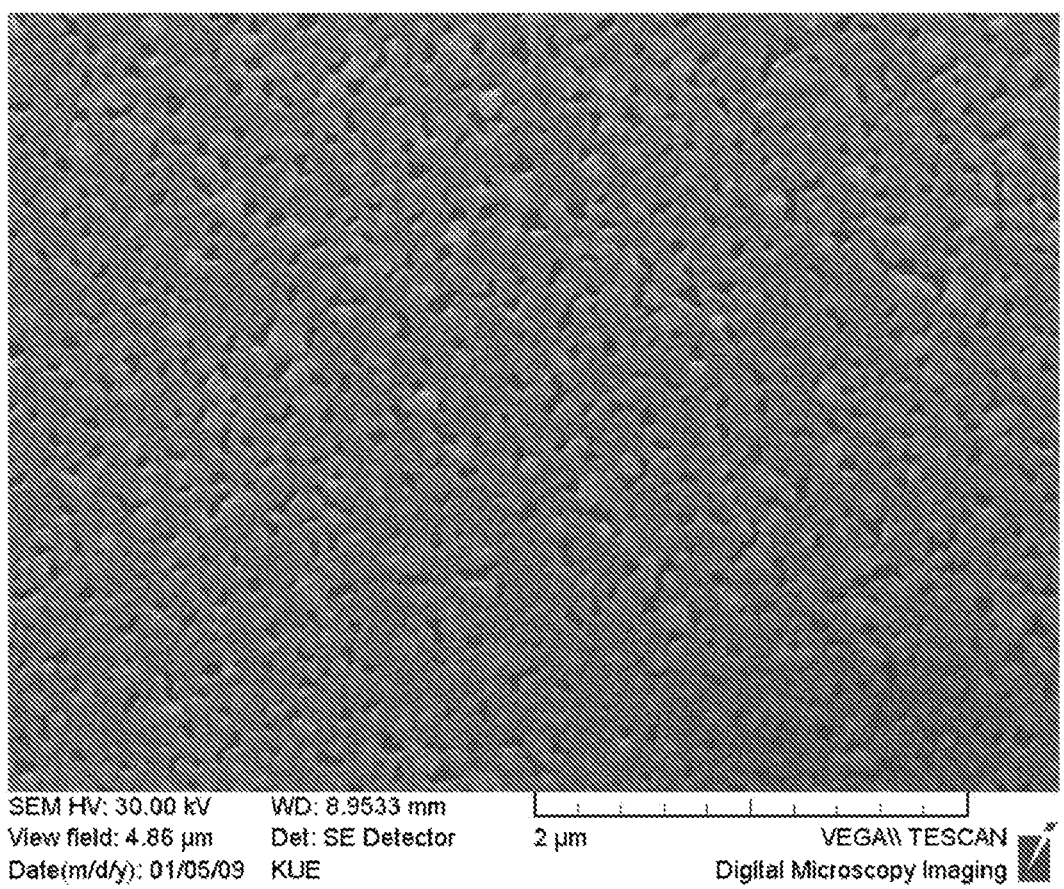
FIG. 6 is an SEM photograph illustrating irregularly arrayed metal nano-holes that can be applied to a TIRF microscope according to an embodiment of the present invention.

FIG. 6 is an SEM photograph illustrating irregularly arrayed metal nano-holes that can be applied to a TIRF microscope according to an embodiment of the present invention. The irregular nano-hole structure illustrated in FIG. 6 can be formed by suitably heating a metal layer (e.g. a Ag layer) formed over a metal thin film.

Figure 7:
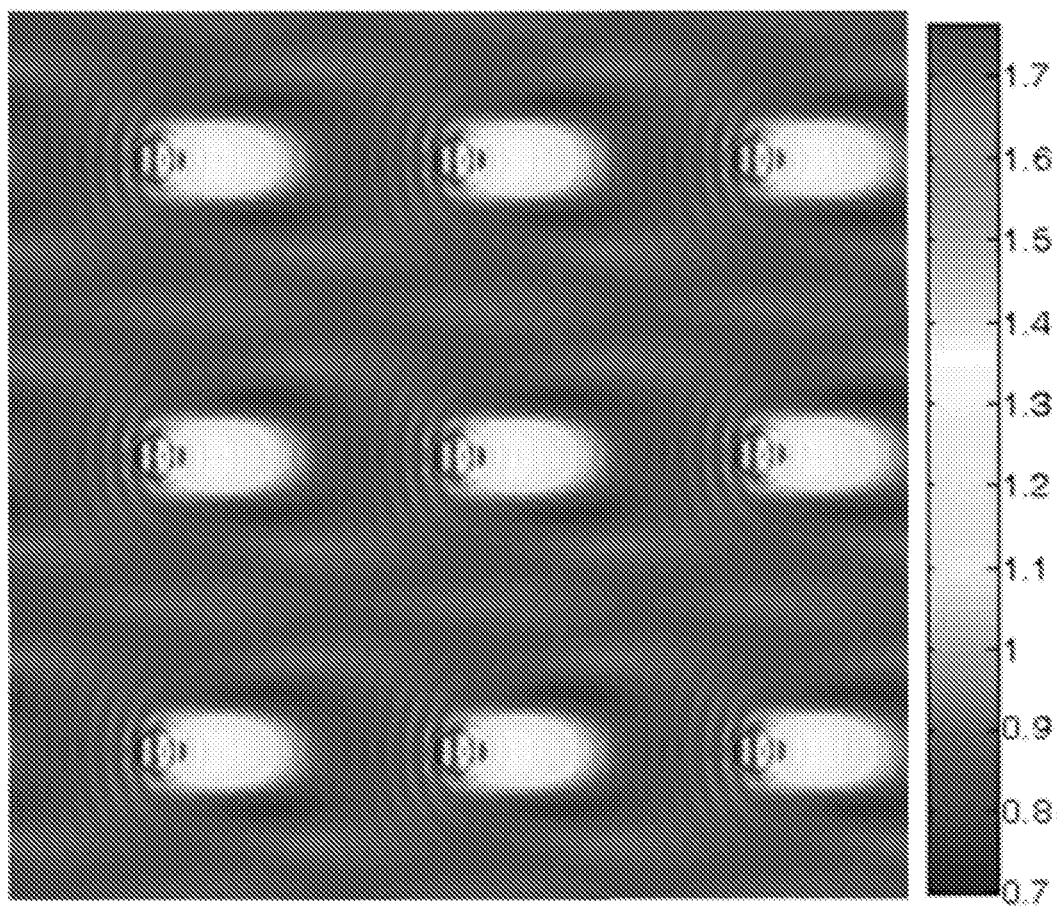
FIG. 7 illustrates the magnetic field intensity of evanescent waves formed during the occurrence of surface plasmon resonance phenomena on the regular multiple nano-hole structure shown in FIG. 4 that can be applied to an embodiment of the present invention.

FIG. 7 illustrates the magnetic field intensity of evanescent waves formed during the occurrence of surface plasmon resonance phenomena on the regular multiple nano-hole structure shown in FIG. 4 that can be applied to an embodiment of the present invention. FIG. 7 illustrates the FDTD calculation results for magnetic field intensity, and the portions indicated in red are where the magnetic field is strongly concentrated. As shown in the drawing, the magnetic fields are strongly localized to the vicinities of the nano-holes, and since the sizes of the localized magnetic fields in the horizontal direction are smaller than the diffraction limit, the images created by the locally concentrated magnetic fields are also smaller than the diffraction limit, thus making it possible to implement a super high resolution.

Figure 8:
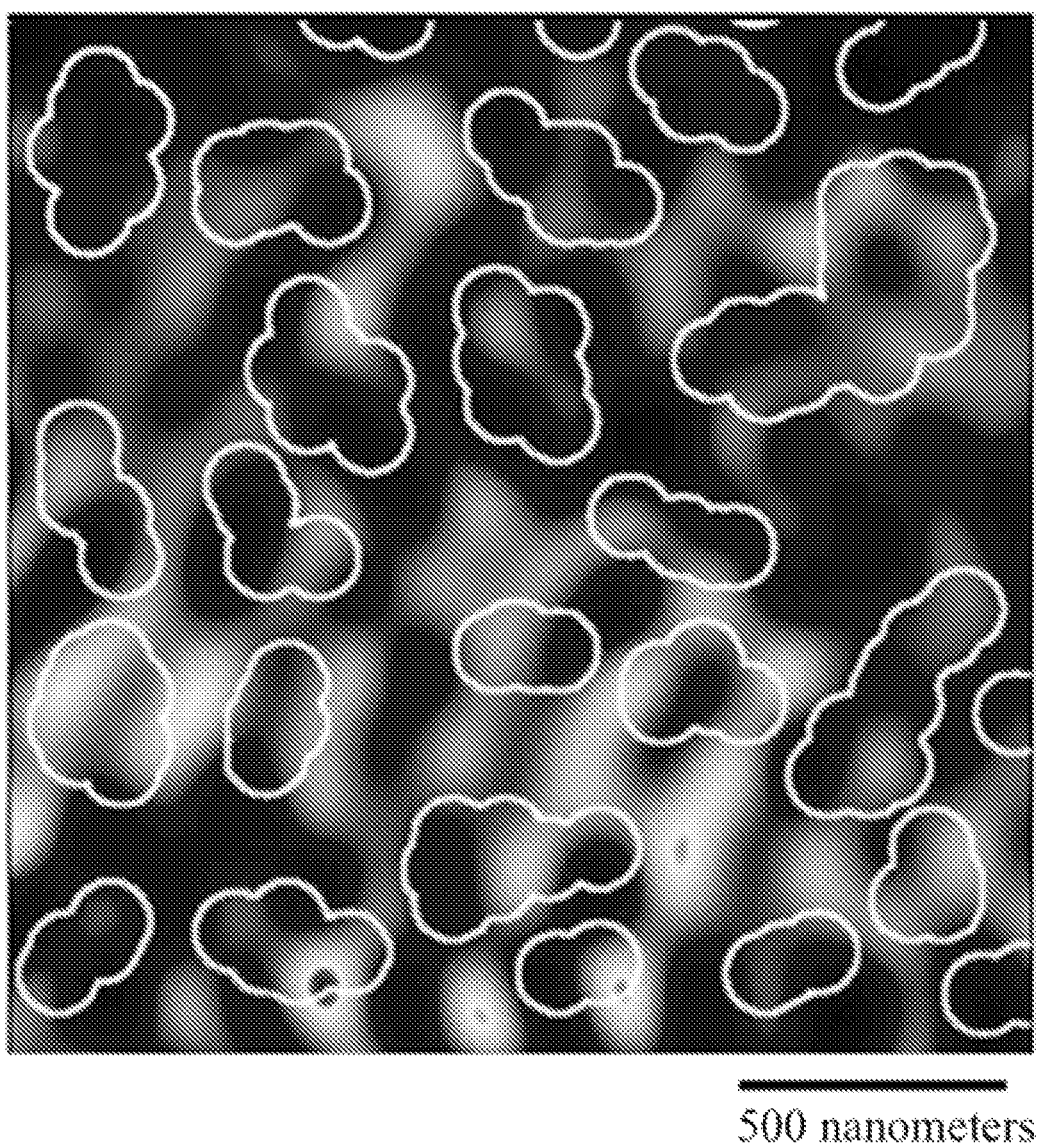
FIG. 8 illustrates the magnetic field intensity of evanescent waves formed during the occurrence of surface plasmon resonance phenomena on an irregular multiple nano-island structure that can be applied to an embodiment of the present invention.

FIG. 8 illustrates the magnetic field intensity of evanescent waves formed during the occurrence of surface plasmon resonance phenomena on an irregular multiple nano-island structure that can be applied to an embodiment of the present invention. As shown in the drawing, the magnetic fields are strongly localized. Although the portions indicated in red (portions where the magnetic fields are strongly concentrated) are formed irregularly unlike FIG. 7, the portions where the magnetic fields are strongly concentrated have sizes in the horizontal direction that are smaller than the diffraction limit, just as in FIG. 7. Thus, the images created by the concentrated magnetic fields are also smaller than the diffraction limit, making it possible to implement a super high resolution.

Figure 9:
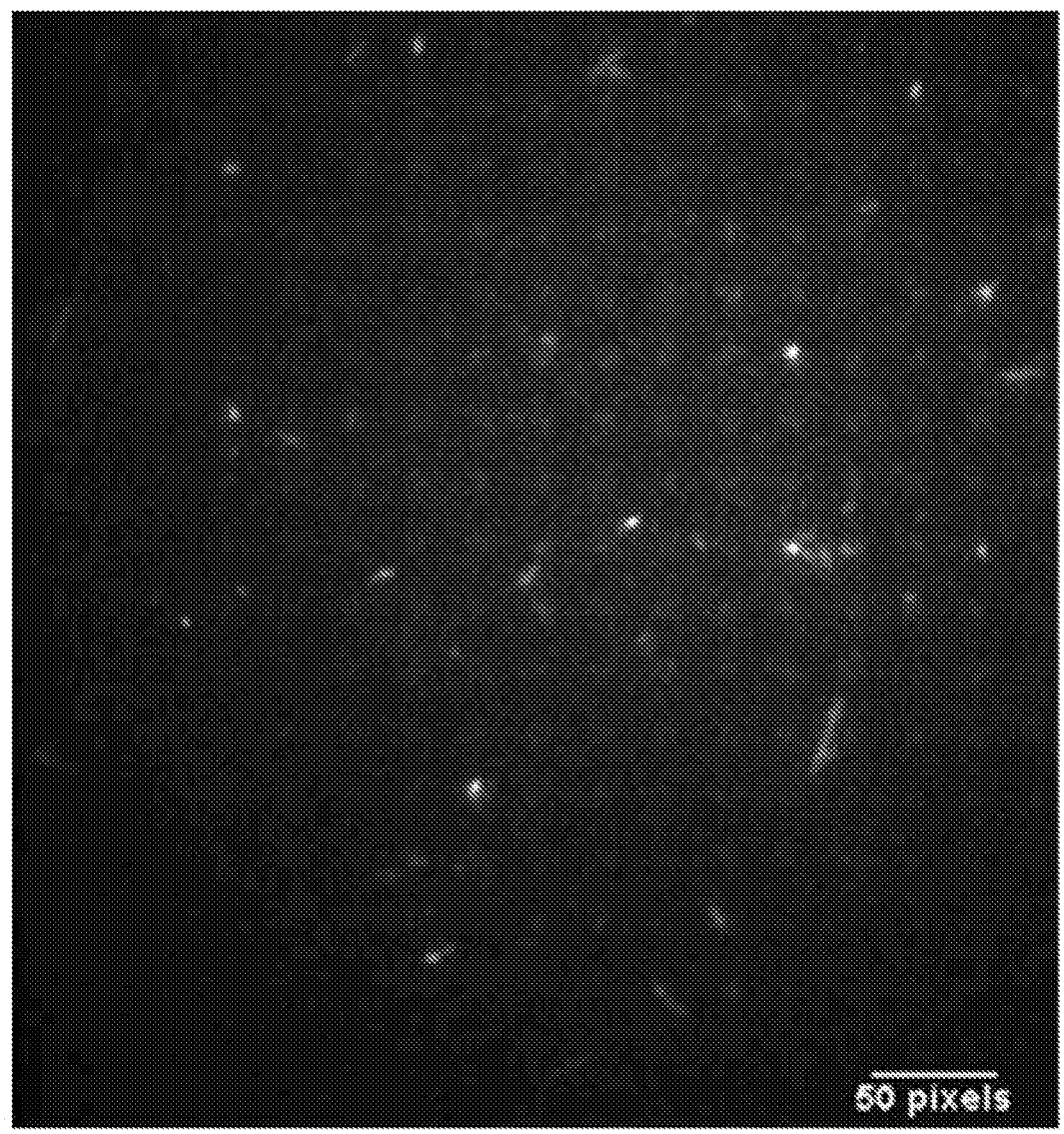
FIG. 9 is an image of microtubules obtained using a TIRF microscope according to an embodiment of the present invention.

FIG. 9 is an image of microtubules obtained using a TIRF microscope according to an embodiment of the present invention. The image of FIG. 9 was obtained by applying a metal nano-hole structure that can generate the surface plasmon resonance phenomenon with incident light under conditions that cause total reflection and can thereby localize the evanescent wave in the vertical direction and the horizontal direction. The image is of microtubules that move using motor proteins, observed using a localized magnetic field distribution such as that illustrated in FIG. 7. As shown in the drawing, the magnetic fields concentrated only at the nano-hole structures have sizes of 100 to 300 nanometers, and the fluorescent image thereby obtained has a very high resolution.

Figure 10:
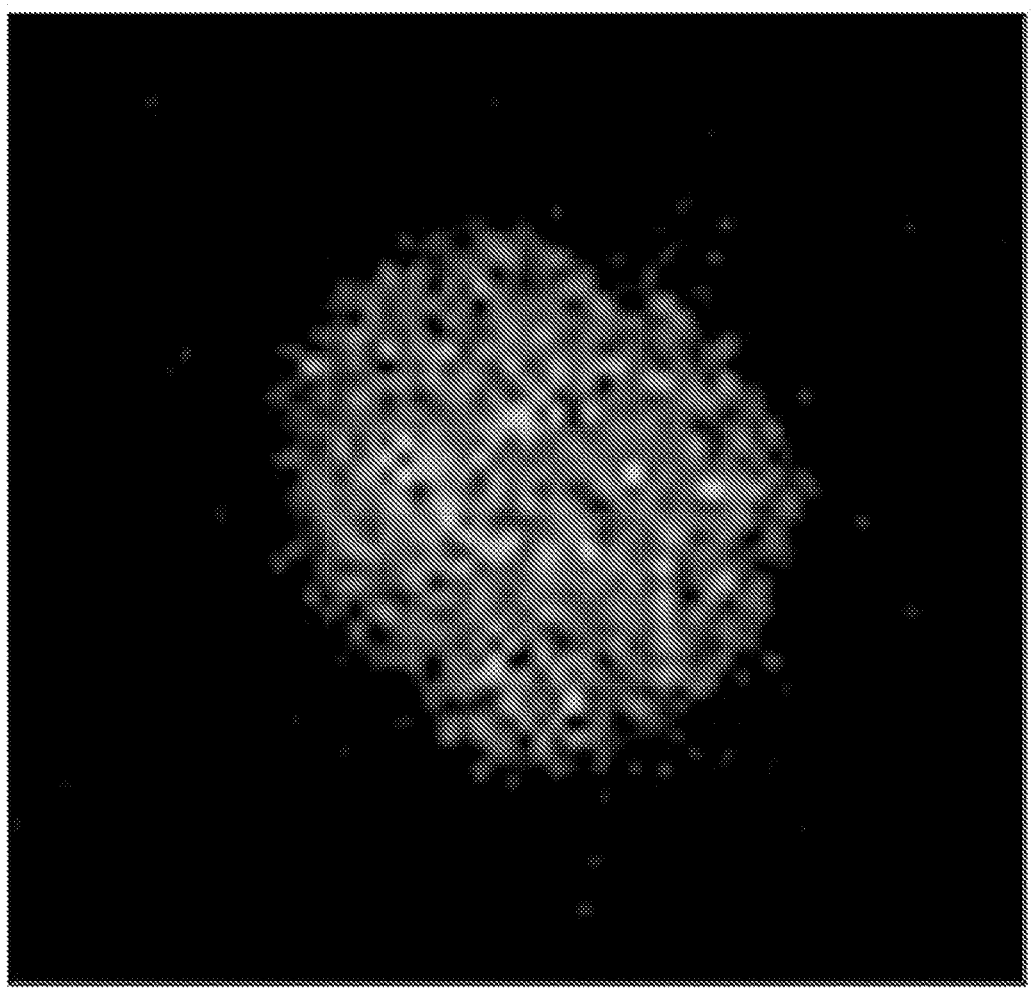
FIG. 10 is an image of a virus applied to an A549 lung cancer cell obtained using a TIRF microscope that does not include a metal nanostructure.
Figure 11:
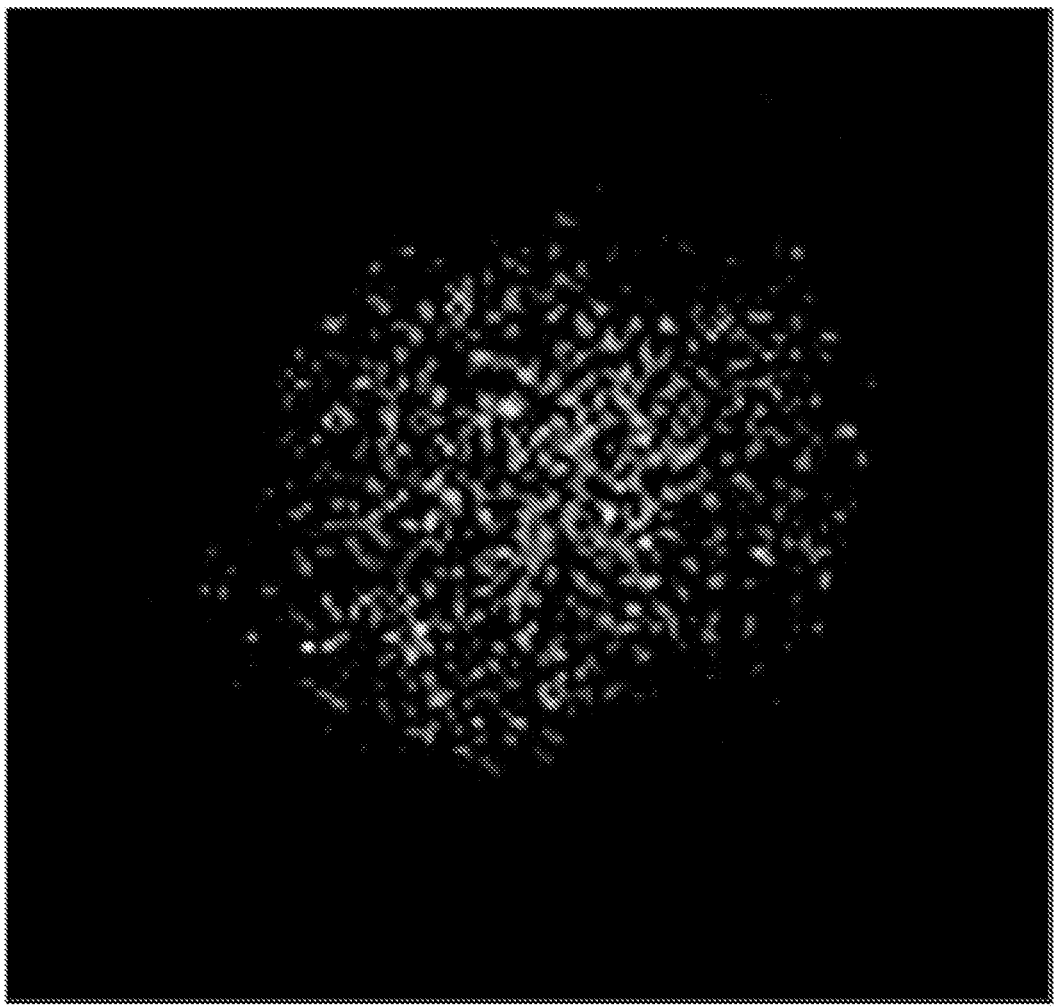
FIG. 11 is an image of a virus applied to an A549 lung cancer cell obtained using a TIRF microscope according to an embodiment of the present invention.

FIG. 10 is an image of a virus applied to an A549 lung cancer cell obtained using a TIRF microscope that does not include a metal nanostructure. The image of FIG. 10 was obtained using an existing optical arrangement (prism, glass substrate, metal layer) that does not include metal nanostructures. In contrast, FIG. 11 shows an image of a virus applied to an A549 lung cancer cell obtained using a TIRF microscope that includes a metal nano-island structure according to an embodiment of the present invention, under the same conditions as for FIG. 10. The metal nano-island structure using in obtaining the image of FIG. 11 can localize evanescent waves in the vertical direction and the horizontal direction by way of the surface plasmon resonance phenomenon for incident light under conditions that cause total reflection. As can be seen in FIG. 10 and FIG. 11, by using a TIRF microscope having an optical arrangement to which the metal nanostructures described above is applied, the resolution in the horizontal direction can be greatly enhanced.

Figure 12:
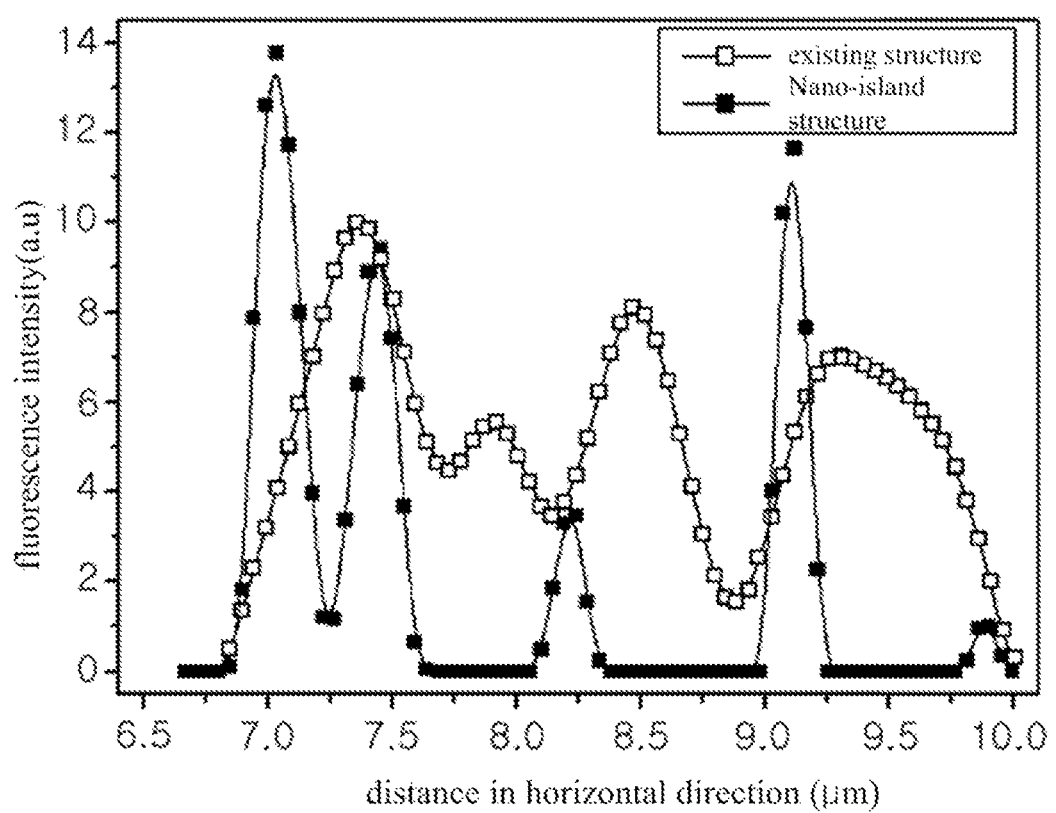
FIG. 12 is a graph representing the fluorescence signals in a particular horizontal-direction area in the images of FIG. 10 and FIG. 11, as converted into quantitative values.

FIG. 12 is a graph representing the fluorescence signals in a particular horizontal-direction area in the images of FIG. 10 and FIG. 11, as converted into quantitative values. As shown in FIG. 12, when the nano-island structure is applied, there is localization in the horizontal direction, resulting in peaks that represent very high fluorescence intensities. Thus, the TIRF microscope to which this nano-island structure is applied can provide enhanced resolution, and the extent of the resolution can be about 100 to 200 nanometers, which are below the diffraction limit.

Figure 13:
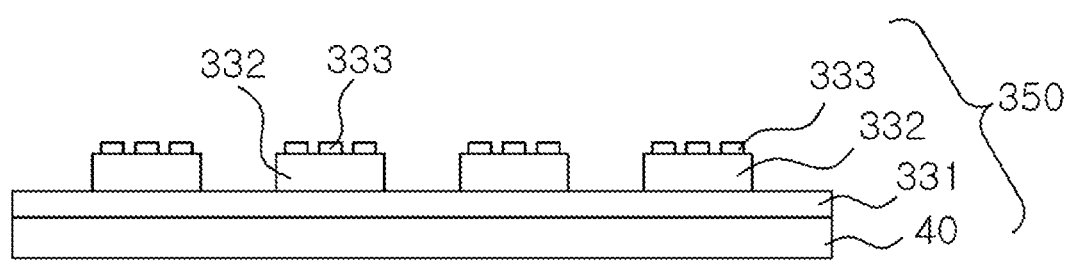
FIG. 13 is a cross-sectional view of a detection module for a TIRF microscope according to an embodiment of the present invention.
Figure 14:
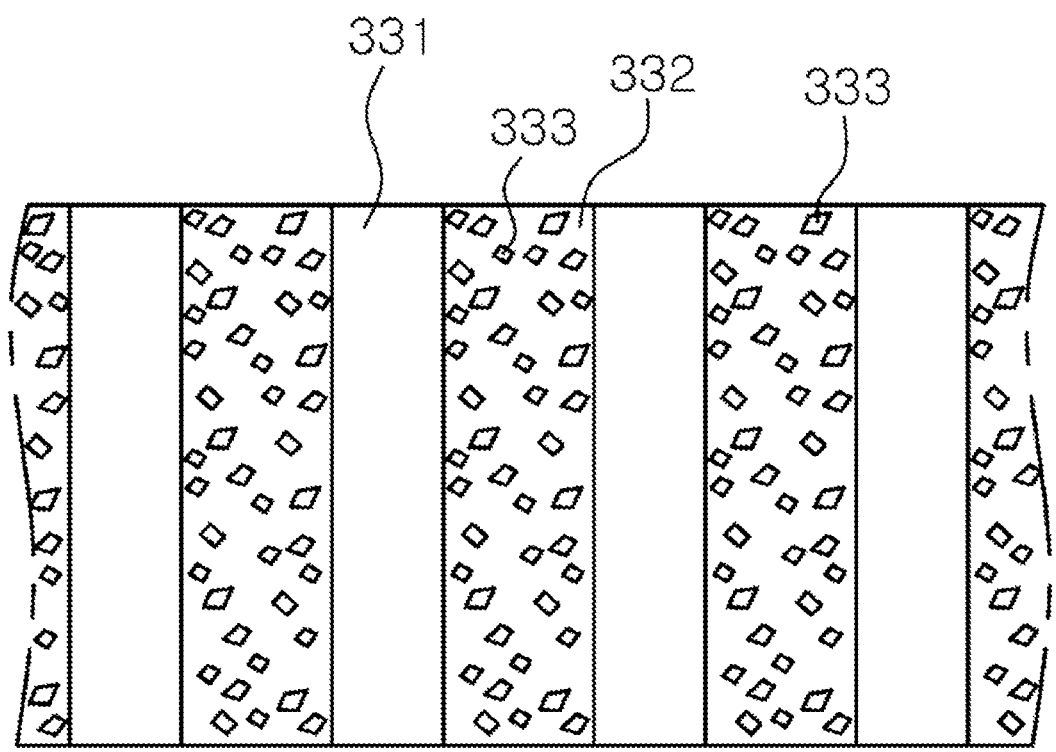
FIG. 14 is a plan view of the detection module of FIG. 13.

FIG. 13 is a cross-sectional view of a detection module for a TIRF microscope according to an embodiment of the present invention, and FIG. 14 is a plan view of the detection module of FIG. 13. In the embodiments of FIGS. 13 and 14, a metal grid may be arranged between the metal thin film and the metal nanostructures, with the nanostructures formed over the metal grid. Referring to FIGS. 13 and 14, the detection module 350 for a TIRF microscope may include a transparent substrate 40, and a metal nanostructure layer 331, 332, 333 formed over the transparent substrate. The metal nanostructure layer may include a metal thin film 331, a metal grid 332 formed over the metal thin film 331, and irregularly arrayed metal nano-islands 333 formed over the metal grid 332. As illustrated in FIG. 14, the metal grid 332 can have multiple stripe-shaped grid structures arrayed parallel to one another over the metal thin film 331. The metal grid 332 can be formed from at least one metal material selected from a group consisting of silver (Ag), gold (Au), platinum (Pt), and aluminum (Al), and can be formed from the same metal material as the metal nano-islands 333.

Figure 15:
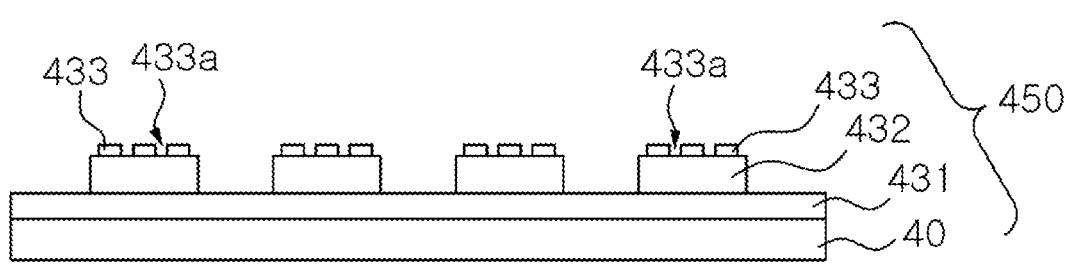
FIG. 15 is a cross-sectional view of a detection module for a TIRF microscope according to another embodiment of the present invention.
Figure 16:
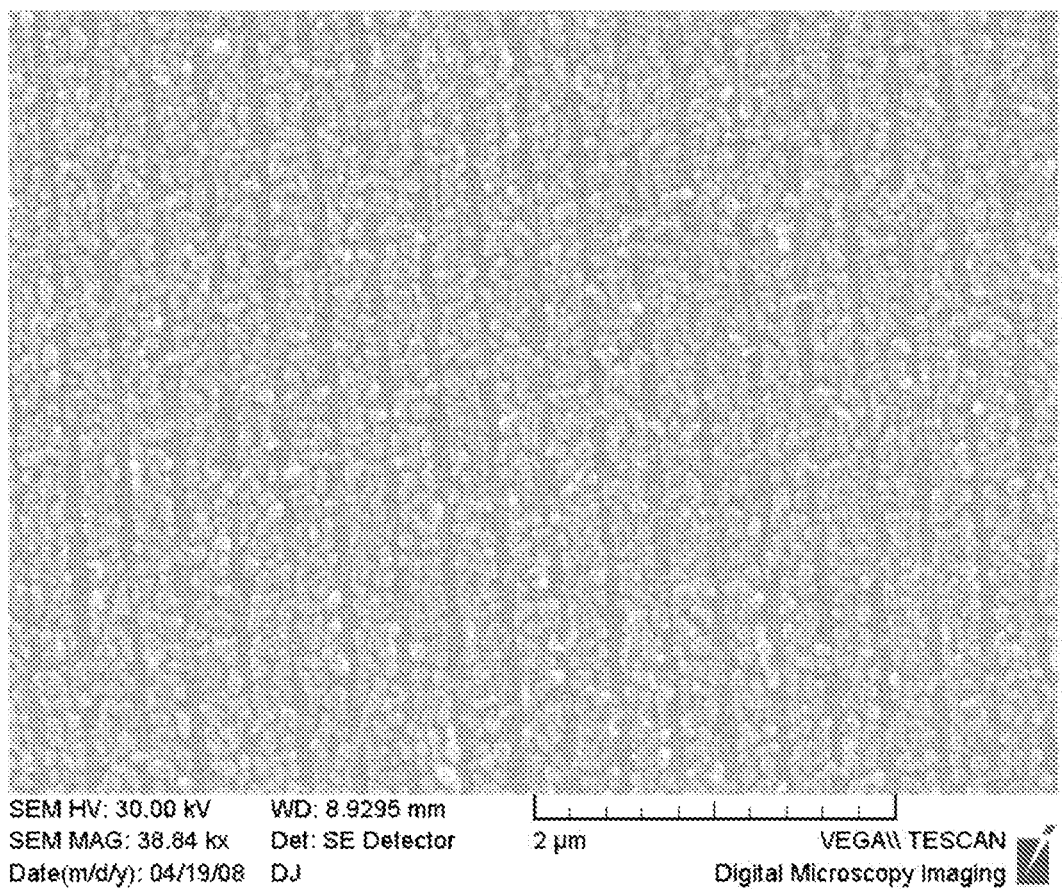
FIG. 16 is an SEM photograph illustrating metal nano-islands arrayed irregularly over a metal grid that can be applied to a TIRF microscope according to an embodiment of the present invention.

FIG. 15 is a cross-sectional view of a detection module for a TIRF microscope according to another embodiment of the present invention. Referring to FIG. 15, the detection module 450 for a TIRF microscope may include a transparent substrate 40, and a metal nanostructure layer 431, 432, 433 formed over the transparent substrate. The metal nanostructure layer may include a metal thin film 431, a metal grid 432 formed over the metal thin film 431, and a metal structure having nano-holes 433a formed over the metal grid 432. The detection module of FIG. 13 or 15 can be used instead of the detection module 50 in FIG. 1 for creating evanescent waves localized in the vertical and horizontal directions. Besides the embodiments of FIGS. 13 and 14, various forms of nanostructures described above, such as irregularly arrayed nano-pillars, regularly arrayed nano-islands, etc., can be arranged over the metal grid. FIG. 16 is an SEM photograph illustrating metal nano-islands arrayed irregularly over a metal grid that can be applied to a TIRF microscope according to an embodiment of the present invention. The nanostructures shown in FIG. 16 can also be applied to the TIRF microscope to obtain an image having high resolution in the horizontal direction.

The descriptions above relate to inducing the surface plasmon resonance localized using the metal nanostructure layer, and to detecting fluorescence images.

According to another embodiment of the present invention, the properties of the incident light can be modified in particular time intervals to further improve the resolution of the TIRF imaging apparatus.

Figure 17:
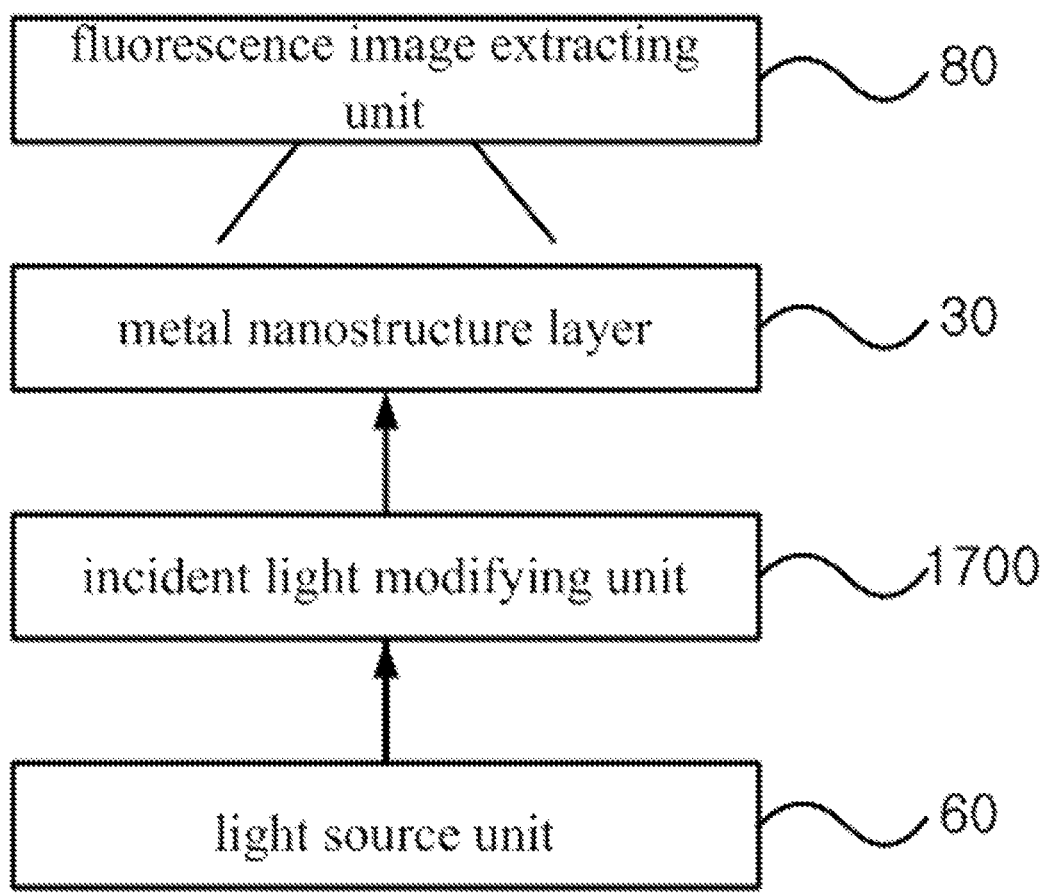
FIG. 17 is a block diagram illustrating a fluorescence imaging apparatus according to another embodiment of the present invention.

FIG. 17 is a block diagram illustrating a fluorescence imaging apparatus according to an embodiment of the present invention.

As shown in FIG. 17, a fluorescence imaging apparatus according to this embodiment can include a metal nanostructure layer 30, a light source unit 60, an incident light modifying unit 1700, and a fluorescence image extracting unit 80.

As the metal nanostructure layer 30, light source unit 60, and fluorescence image extracting unit 80 have already been described above, the description of these components will be omitted here.

Figure 18:
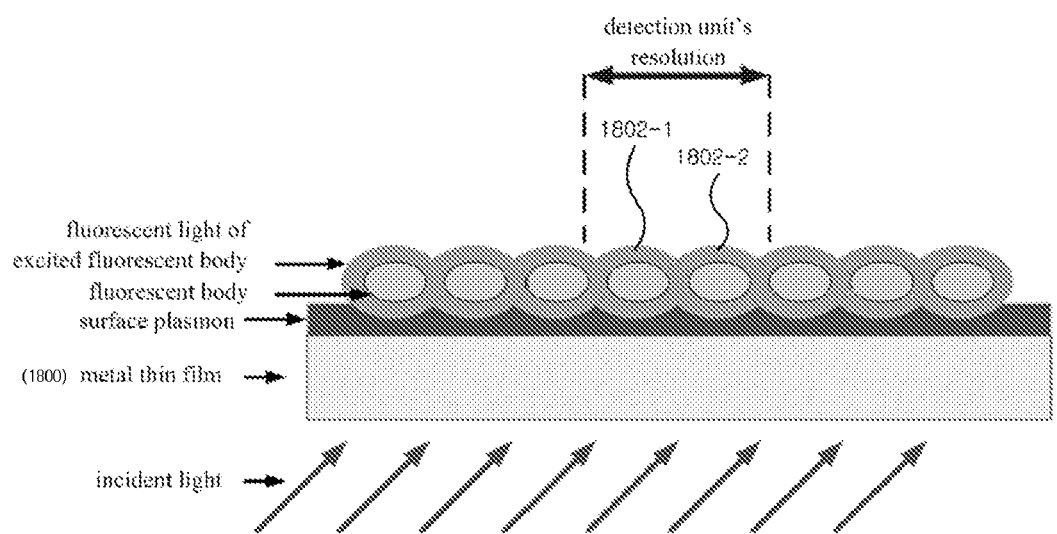
FIG. 18 illustrates the principles of a typical TIRF microscope.

FIG. 18 illustrates the principles of a typical TIRF microscope. As shown in FIG. 18, incident light may be provided to a metal thin film 1800 that does not include multiple nanostructures; surface plasmon resonance is generated over the metal thin film; and as a result, excited fluorescent bodies 1802 are provided over the metal thin film.

In general, a fluorescence image extracting unit 80 has a preset resolution in the horizontal direction that can be calculated by Abbe's diffraction equation. Under the resolution conditions illustrated in FIG. 18, if there are a multiple number of excited fluorescent bodies over the metal thin film 1800, there may be a problem of the fluorescence image extracting unit 80 being unable to differentiate adjacent fluorescent bodies 1802-1, 1802-2 (see FIG. 21a).

Figure 19:
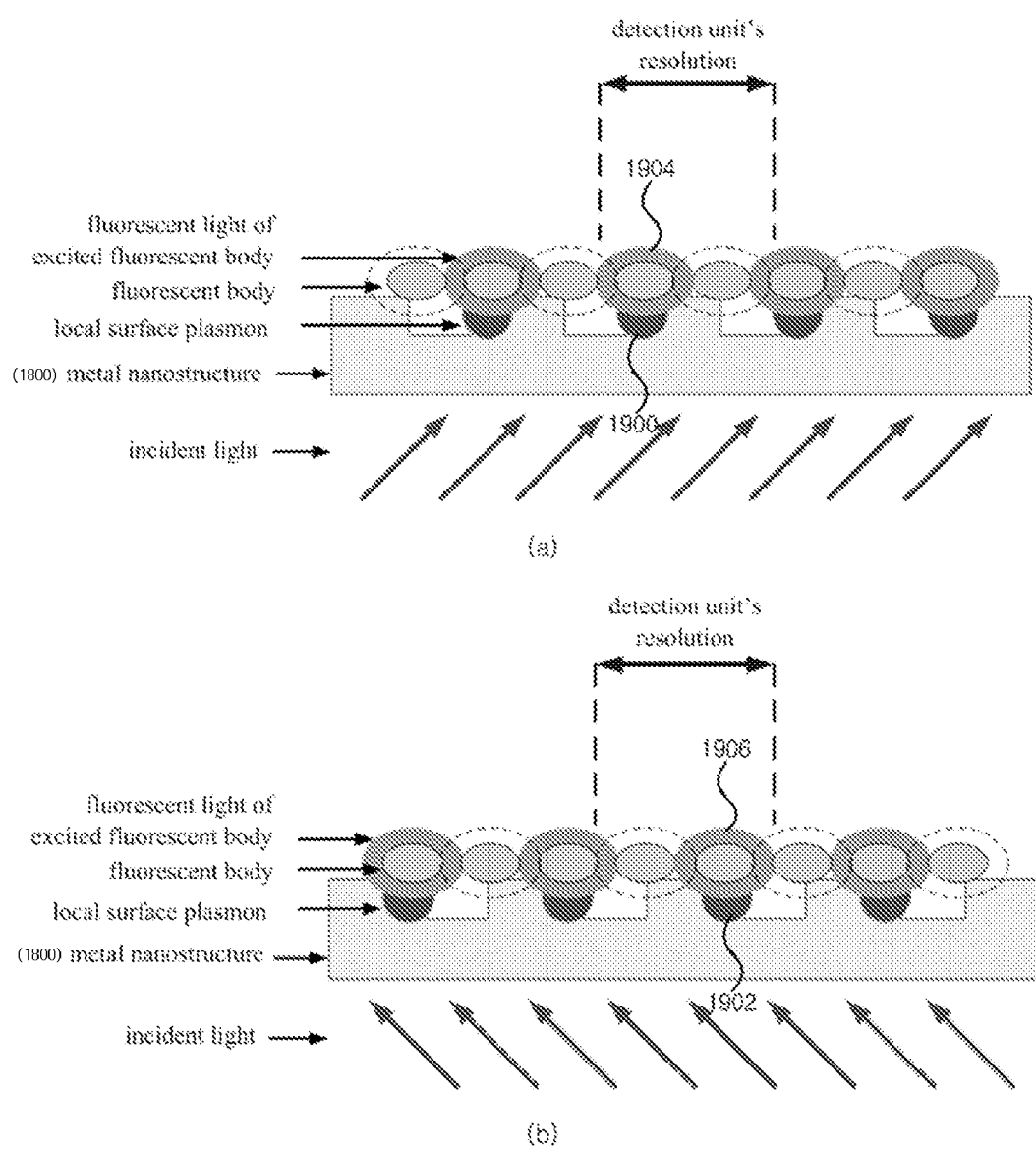
FIG. 19 illustrates local surface plasmon resonance for cases in which the incident light is provided in different incident angles according to another embodiment of the present invention.

FIG. 19 illustrates local surface plasmon resonance for cases in which the incident light is provided in different incident angles according to another embodiment of the present invention.

FIG. 19 illustrates an example in which the multiple nanostructures are nano-holes. When the metal nanostructure layer 30 is composed of multiple nanostructures as in FIG. 19, the surface plasmon resonance can be generated for local areas, unlike FIG. 18, and it is possible to selectively excite only the fluorescent bodies positioned in the local areas.

Figure 21:
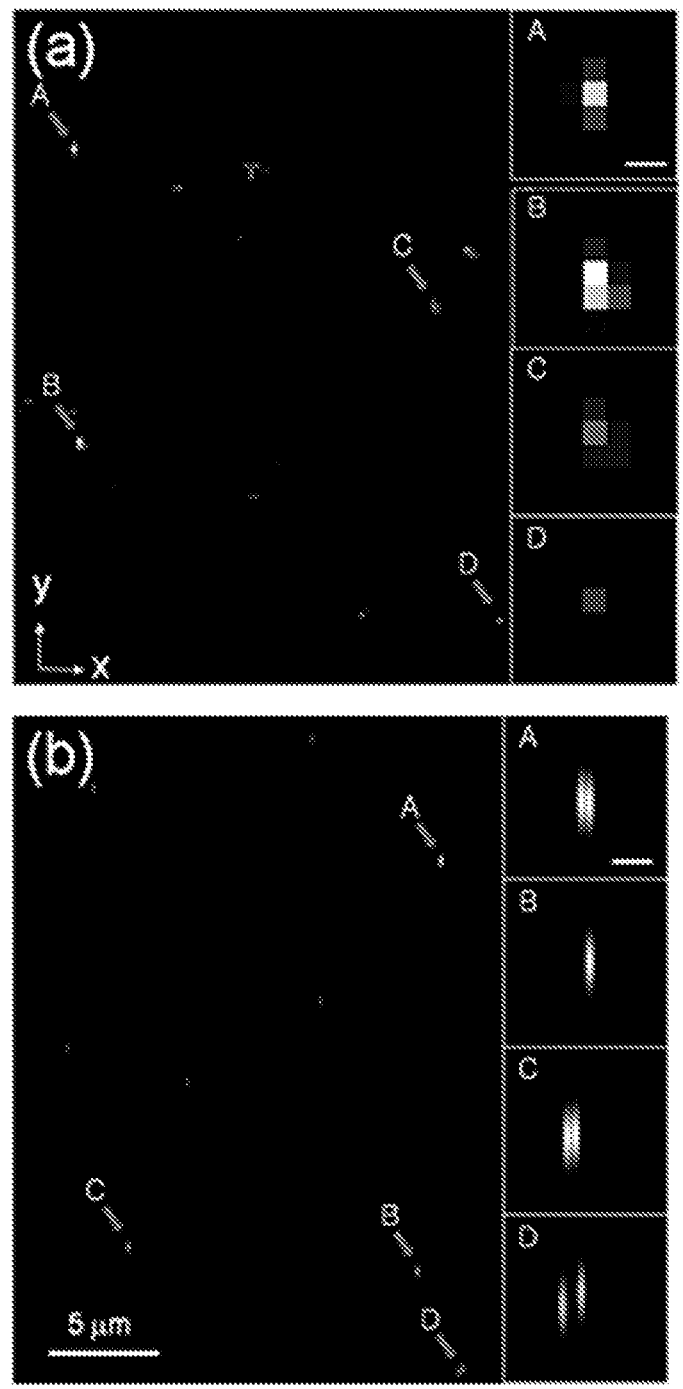
FIG. 21 shows fluorescence images detected by using a TIRF imaging apparatus according to another embodiment of the present invention.

According to another embodiment of the present invention, the direction of incidence of the incident light can be differed, as illustrated in drawings (a) and (b) of FIG. 19, in order to selectively excite fluorescent bodies 1904, 1906 positioned in different local areas 1900, 1902 of the nanostructures (see FIG. 21b).

FIG. 21b shows a fluorescence image detected when there are fluorescent bodies present at both edges 1900, 1902 of a nanostructure, as in FIG. 19. By providing different directions of incidence as in this embodiment, the fluorescent bodies positioned at either edge can be selectively excited, unlike the case for FIG. 21a, so that a high resolution image may be obtained.

In this case, only some of the fluorescent bodies positioned over the metal nanostructure layer 30 are excited, and consequently, the same results can be obtained as enhancing the resolution of the fluorescence image extracting unit 80.

According to this embodiment, the incident light modifying unit 1700 may modify the properties of the incident light emitted from the light source unit 60, to provide incident light with different directions of incidence (L1, L2) to the metal nanostructure layer 30, as in FIG. 19.

Although the above illustrates the incident light modifying unit 1700 as modifying the direction of incidence, the present invention is not thus limited, and the incident light modifying unit 1700 can also modify the incidence angle or wavelength of the light source unit 60, to thereby generate surface plasmon resonance in various local areas of the metal nanostructure layer 30.

Figure 20:
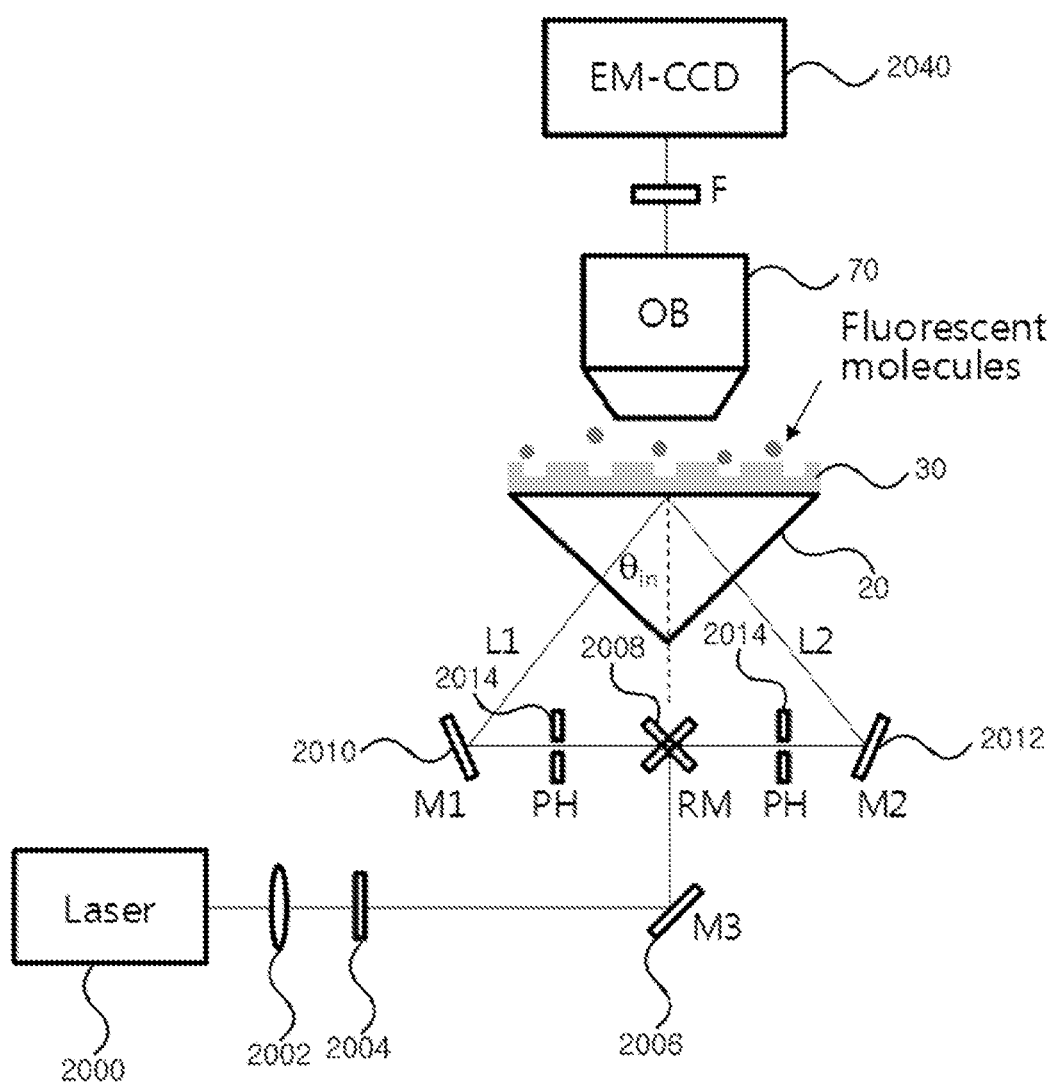
FIG. 20 illustrates the detailed structure of a fluorescence imaging apparatus according to another embodiment of the present invention.

FIG. 20 illustrates the detailed structure of a fluorescence imaging apparatus according to an embodiment of the present invention.

FIG. 20 illustrates the structure of a fluorescence imaging apparatus for providing two types of incident light having different directions of incidence onto the metal nanostructure layer 30 as in FIG. 19.

As shown in FIG. 20, the fluorescence imaging apparatus according to this embodiment can include a laser emitting unit 2000 corresponding to the light source unit 60, a beam expander 2002, and a polarizer 2004.

A laser beam (incident light) of a particular wavelength may be emitted through the laser emitting unit 2000, and the incident light may pass through the beam expander 2002, to be polarized into a TM (transverse magnetic) mode by the polarizer 2004.

According to this embodiment, the incident light outputted from the polarizer 2004 may pass through the incident light modifying unit 1700 and may arrive at the metal nanostructure layer 30 positioned over the prism 20.

In order to provide the incident light to the metal nanostructure layer 30 with different directions of incidence, the incident light modifying unit 1700 can include a first minor 2006, a rotary minor 2008, a second minor 2010, and a third mirror 2012.

Here, the first minor 2006 may reflect the incident light outputted from the polarizer 2004 towards the rotary minor 2008. The rotary minor 2008 may reflect the incident light reflected by the first minor 2006 in a first direction or a second direction.

The rotary minor 2008 can be connected with a drive unit and a timer (not shown), and the drive unit may cooperate with the timer to rotate the rotary minor 2008 in preset time intervals.

Here, the laser emitting unit 2000 can output a light source every time the rotation of the rotary minor 2008 is completed.

In FIG. 20, the first direction may be defined as the leftward direction, i.e. the direction in which the second minor 2010 is positioned, while the second direction may be defined as the rightward direction, i.e. the direction in which the third minor 2012 is positioned.

The second minor 2010 may be positioned in the first direction such that the incident light reflected by the rotary minor 2008 may be reflected to the prism 20.

Also, the third minor 2012 may be positioned in the second direction such that the incident light reflected by the rotary minor 2008 may be reflected to the prism 20.

Preferably, pin holes 2014 can be additionally arranged between the rotary minor 2008 and the second minor 2010 and the third minor 2012, respectively.

According to this embodiment, the rotary minor 2008 may rotate in preset time intervals, so that the incident light may be reflected in the first direction or the second direction.

Because of such time difference, at a first instance, the incident light can arrive at the metal nanostructure layer 30 via the first minor 2006, rotary minor 2008, and second minor 2010 in a first direction of incidence (L1), and at a second instance after a preset duration of time from the first instance, the incident light can arrive at the metal nanostructure layer 30 via the first minor 2006, rotary minor 2008, and third minor 2012 in a second direction of incidence (L2).

When the metal nanostructure layer 30 has a nano-hole structure as in FIG. 19, if the incident light has a first direction of incidence (L1), the surface plasmon resonance may be generated in the first local area 1900, and the fluorescent bodies positioned in the first local area may be excited.

If the incident light has a second direction of incidence (L2), the surface plasmon resonance may be generated in the second local area 1902, and the fluorescent bodies positioned in the second local area may be excited, so that the fluorescence signals may be detected by the fluorescence image extracting unit 80.

The fluorescence image extracting unit 80 can include an object lens 70 and an image-capturing element 2040, and fluorescence signals emitted by the excitation of fluorescent bodies can pass through the object lens 70 and a band-pass filter (not shown) for enhancing contrast sensitivity, and afterwards can be detected in a 2-dimensional form by the image-capturing element 2040.

Although it is not illustrated in FIG. 20, a transparent substrate can be additionally provided between the prism 20 and the metal nanostructure layer 30.

Here, the transparent substrate and the prism 20 can be made of the same material, and a metal film for enhancing adhesion, such as a chromium (Cr) film, for example, can be additionally included between the transparent substrate and the metal nanostructure layer 30.

For the present embodiment, the transparent substrate and the metal nanostructure layer 30 formed over the transparent substrate can be provided in the form of an independent part, as a detection module for a fluorescence imaging apparatus.

In the fluorescence imaging apparatus of FIG. 20, it is also possible to omit the prism 20 and instead arrange the object lens 70 at the position of the prism 20. For example, an object lens 70 having a numerical aperture of 0.8 or higher can be arranged under the transparent substrate (with the prism omitted) to totally reflect the incident light. In this case, the image-capturing element 2040 may be arranged under the object lens 70 and may detect the fluorescent signal emitted due to the evanescent wave localized in the vertical and horizontal directions from under the transparent substrate.

Industrial Applicability

The present invention is not to be limited by the embodiments described above and the accompanying drawings. The scope of rights is to be limited by the appended claims, where it will be apparent to those of ordinary skill in the art that various substitutions, alterations, and modifications can be made without departing from the spirit of the present invention as defined by the claims.

The invention claimed is:

1. A total internal reflection fluorescence imaging apparatus, comprising:
   a metal nanostructure layer including a metal thin film and a nanostructure formed on the metal thin film;
   a light source unit configured to provide incident light such that the incident light is totally reflected off the metal nanostructure layer and an evanescent wave localized in a horizontal direction of the light source unit is created between the metal nanostructure layer and a biological specimen arranged on the metal nanostructure layer; and
   a fluorescence image extracting unit configured to extract and image a fluorescence signal generated by the biological specimen due to the evanescent wave localized in a horizontal direction of the fluorescence image extracting unit,
   wherein the metal nanostructure layer further comprises a metal grid formed over the metal thin film, and a plurality of nanostructures are formed over the metal grid.

2. The total internal reflection fluorescence imaging apparatus of claim 1, further comprising:
   an incident light modifying unit configured to modify a property of the incident light,
   wherein the property of the incident light includes at least one of an incident angle, and a wavelength of the incident light.

3. The total internal reflection fluorescence imaging apparatus of claim 2, wherein the incident light modifying unit is configured to provide incident light of different properties onto the metal nanostructure layer in preset time intervals.

4. The total internal reflection fluorescence imaging apparatus of claim 2, wherein the incident light modifying unit comprises:
   a first minor configured to reflect the incident light emitted from the light source unit;
   a rotary mirror configured to reflect the incident light reflected by the first minor in a first direction or a second direction by way of rotation;
   a second minor positioned in the first direction and configured to reflect the incident light reflected by the rotary minor towards the metal nanostructure layer; and
   a third minor positioned in the second direction and configured to reflect the incident light reflected by the rotary minor towards the metal nanostructure layer.

5. The total internal reflection fluorescence imaging apparatus of claim 1, further comprising:
   a transparent substrate arranged underneath the metal thin film; and
   a prism arranged underneath the transparent substrate.

6. The total internal reflection fluorescence imaging apparatus of claim 1, wherein the nanostructure comprises at least one of a plurality of nano-wires, nano-islands, nano-pillars, and nano-holes arrayed irregularly over the metal thin film.

7. The total internal reflection fluorescence imaging apparatus of claim 1, wherein the nanostructure comprises at least one of a plurality of nano-wires, nano-islands, nano-pillars, and nano-holes arrayed regularly in constant intervals over the metal thin film.

8. The total internal reflection fluorescence imaging apparatus of claim 1, wherein the metal nanostructure layer is formed from at least one metal material selected from a group consisting of silver (Ag), gold (Au), platinum (Pt), and aluminum (Al).

9. The total internal reflection fluorescence imaging apparatus of claim 1, wherein the nanostructure and the metal thin film are formed from a same metal material.

10. The detection module of claim 1, wherein the metal grid comprises a plurality of stripe-shaped grid structures arrayed parallel to one another over the metal thin film.

11. The total internal reflection fluorescence imaging apparatus of claim 1, wherein the metal grid comprises a plurality of stripe-shaped grid structures arrayed parallel to one another over the metal thin film.

12. The total internal reflection fluorescence imaging apparatus of claim 1, wherein the metal grid is formed from at least one metal material selected from a group consisting of silver (Ag), gold (Au), platinum (Pt), and aluminum (Al).

13. The total internal reflection fluorescence imaging apparatus of claim 1, wherein the plurality of nanostructures and the metal grid are formed from a same metal material.

14. A detection module comprising a metal nanostructure layer, the metal nanostructure layer having a metal thin film and a nanostructure formed on the metal thin film, wherein incident light is totally reflected off the metal nanostructure layer so that an evanescent wave localized in a horizontal direction of the metal nanostructure layer is created between the metal nanostructure layer and a biological specimen arranged on the metal nanostructure layer, wherein the metal nanostructure layer further comprises a metal grid formed over the metal thin film, and a plurality of nanostructures are formed over the metal grid.

15. The detection module of claim 14, wherein the nanostructure comprises at least one of a plurality of nano-wires, nano-islands, nano-pillars, and nano-holes arrayed irregularly over the metal thin film.

16. The detection module of claim 14, wherein the nanostructure comprises at least one of a plurality of nano-wires, nano-islands, nano-pillars, and nano-holes arrayed regularly in constant intervals over the metal thin film.

17. The detection module of claim 14, wherein the metal nanostructure layer is formed from at least one metal material selected from a group consisting of silver (Ag), gold (Au), platinum (Pt), and aluminum (Al).

18. The detection module of claim 14, wherein the nanostructure and the metal thin film are formed from a same metal material.

* * * * *